United States Patent [19]
Dhar et al.

[11] Patent Number: 5,453,509
[45] Date of Patent: Sep. 26, 1995

[54] FUNCTIONALIZATION OF ACYL PYRIDINIUM SALTS

[75] Inventors: T. G. Murali Dhar, River Edge; Charles Gluchowski, Wayne, both of N.J.

[73] Assignee: Synaptic Pharmaceutical Corporation, Paramus, N.J.

[21] Appl. No.: 134,179

[22] Filed: Oct. 8, 1993

[51] Int. Cl.$^6$ .................... C07D 211/80; C07D 215/14; C07D 217/06
[52] U.S. Cl. .................... 546/14; 546/156; 546/147; 546/168; 546/298; 546/314; 546/328
[58] Field of Search .................... 546/156, 168, 546/298, 314, 14, 147, 328

OTHER PUBLICATIONS

Akiba, K. et al., "Addition of Trimethylsilyl Enol Ethers to Quinolinium Salts: A Facile Synthesis of Methyl 2–(2–Oxoalkyl)–1,2–Dihydroquinoline–1–Carboxylates and Their Cyclization," Heterocycles (Jul. 1984), vol. 22, pp. 1519–1522.

Comins, D. L. et al., "Regioselective Substitution in Aromatic Six–Membered Nitrogen Heterocycles," in Advances in Heterocyclic Chemistry, Katritzky, A. R., editor; Academic Press, Inc.; New York (1988), vol. 44, pp. 199–267.

Courtois, G. et al., "Addition regioselective d'organometalliques alpha–insatures ou alpha–fonctionnels au chlorure de N–ethoxycarbonylpyridinium: synthese de dihydro–1,2 (ou–1,4)pyridines 2–(–ou 4–)substituees," Tetrahedron Letters (1985), vol. 26, No. 8, pp. 1027–1030.

Comins, D. L. et al., "Regioselective Addition of Titanium Enolates to 1–Acylpyridinium Salts. A Convenient Synthesis of 4–(2–Oxoalkyl) Pyridines" in Tetrahedron Letters (1984), vol. 25, No. 31, pp. 3297–3300.

Yamaguchi, R. et al., "Reaction of Allylic Tin Reagents with Nitrogen Heteroaromatics Activated by Alkyl Chloroformates: Regioselective Synthesis of alpha–Allylated 1,2–Dihydropyridines and Change of the Regioselectivity Depending on Methyl Substituents at the Allylic Moiety," in Journal of the American Chemical Society (1988), vol. 53, pp. 3507–3512.

Comins, D. L. et al., "Regioselective Addition of Grignard Reagents to 1–Acylpyridinium Salts. A Convenient Method for the Synthesis of 4–Alkyl(aryl)pyridines," Journal of Organic Chemistry (1982), vol. 47, pp. 4315–4319.

Akiba, K. et al., "A Convenient Method for the Regioselective Synthesis of 4–Alkyl (aryl)pyridines Using Pyridinium Salts," Bulletin of the Chemical Society of Japan (1984), vol. 57, pp. 1994–1999.

Zapata, A. and Acuna, C. A., "A Convenient Synthesis of alpha–Tributylstannyl Esters," Synthetic Communications (1984), vol. 14, pp. 27–32.

*Primary Examiner*—C. Warren Ivy
*Assistant Examiner*—Zinna N. Davis
*Attorney, Agent, or Firm*—John P. White

[57] ABSTRACT

This invention relates to a method of preparation of 1,2-dihydropyridine compounds having the structure:

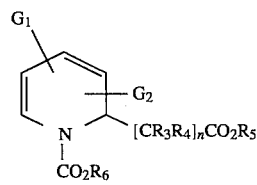

which comprises reacting a compound having the structure:

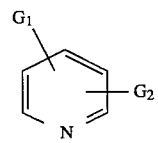

The reaction is performed under suitable reaction conditions and in an appropriate solvent so as to form the 1,2-dihydropyridine compound. In a similar manner 1,2-dihydroquinolines, dihydroisoquinolines, dihydropyridones, dihydroquinolones and dihydroisoquinolones may also be prepared. The invention is also directed to compounds prepared by this method.

35 Claims, No Drawings

FUNCTIONALIZATION OF ACYL PYRIDINIUM SALTS

BACKGROUND OF THE INVENTION

This invention relates to the functionalization of acylpyridinium salts in a chemoselective and regioselective manner. A problem faced in such syntheses involves introducing a carboalkoxyalkyl group regio and chemoselectively onto a functionalized pyridine ring system. There have been isolated reports of the addition of a carboethoxymethyl group to a unsubstituted pyridine ring employing either the Reformatsky reagent derived from ethyl bromoacetate or the titanium enolate of ethyl acetate to yield a mixture of 1,2 and 1,4 dihydropyridines in moderate yield[2a,b]. However, chemoselectivity is a problem with these reagents because of their tendency to add to carbonyl compounds (vide infra).

Other workers[1,9] have used Grignard reagents to prepare 1,2 dihydropyridines, however chemoselectivity is a problem because such reagents also tend to add to carbonyl compounds.

A report by Yamaguchi et.al.,[3] demonstrated that allyltin reagents are sufficiently nucleophilic to add to acyl pyridinium salts in a regio and chemospecific manner.

SUMMARY OF THE INVENTION

This invention relates to a method of preparation of 1,2-dihydropyridine compounds having the structure:

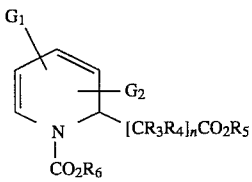

which comprises reacting a compound having the structure:

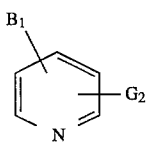

with $(R_2)_3Sn(CR_3R_4)_nCO_2R_5$ and $XCO_2R_6$.

The reaction is performed under suitable reaction conditions and in an appropriate solvent so as to form the 1,2-dihydropyridine compound. In a similar manner 1,2 dihydroquinolines, dihydroisoquinolines, dihydropyridones, dihydroquinolones and dihydroisoquinolones may also be prepared. The first invention also directed to compounds prepared by this method.

DETAILED DESCRIPTION OF THE INVENTION

The present invention provides a method of preparing a 1,2-dihydropyridine compound having the structure:

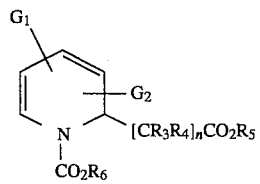

In each compound each $G_1$ $G_2$ and $G_3$ may independently be H, CHO, biphenyl, benzhydryl, $R_1CO$ or aryl which may be unsubstituted or substituted with halogen, triflouromethyl, methoxy, nitro, amino, aldehyde, nitrile, ester, trimethylsilyl, triethylsilyl, tert-butyldimethylsilyl, triisopropylsilyl, trimethyltin, triethyltin, triisopropyltin. $R_1$ may be $C_3$–$C_8$ cycloalkyl, thienyl, aryl, or furan which may be unsubstituted or substituted with halogen, $C_1$–$C_{16}$ alkyl which may be straight chain or branched, trifluoromethyl, methoxy, nitro, amino, aldehyde, nitrile, ester. $R_3$, $R_4$ may be H, $C_1$–$C_{10}$ alkyl and $R_5$ may be $C_1$–$C_6$ straight chain or branched alkyl, aryl, 2,2,2-trichloroethyl, trimethylsilyl, tert-butyldimethylsilyl and n is an integer from 1 to 16. $R_6$ may be a $C_1$–$C_6$ alkyl which may be straight chain or branched, aryl, benzyl, p-methoxybenzyl, allyl, trichloromethyl, menthyl (+ or –).

To prepare the compounds above the method provides reacting a compound having the structure:

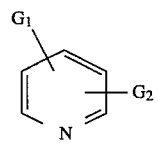

wherein $G_1$ and $G_2$ are as defined above;

with a compound having the structure:

$R_2$ may be a $C_1$–$C_4$ alkyl which may be straight chain or branched and n, $R_3$, $R_4$, $R_5$ are as defined above and with a compound having the structure:

X may be a halogen and $R_6$ is as defined above, so as to form the 1,2-dihydropyridine compound.

The invention also provides a method of preparing a 1,2-dihydroquinoline compound having the structure:

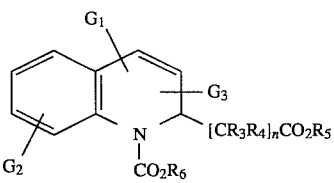

in a parallel manner to the 1,2 dihydropyridine compounds above.

The invention further provides a method of preparing a 1,2-dihydroisoquinoline compound having the structure:

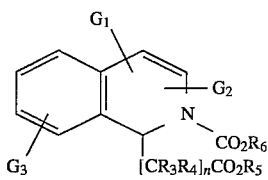

using the method described above.

The invention also provides a method of preparing a 1,2-dihydropyridone compound having the structure:

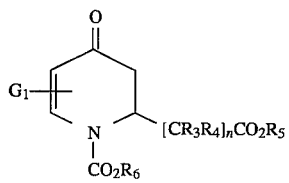

by reacting a compound having the structure:

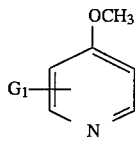

as in the method described above.

The invention provides a method of synthesizing 1,2-dihydroquinolone compound having the structure:

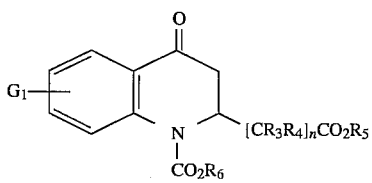

as in the method described above.

In addition, the methods herein may also be use with 7,8 benzoquinoline, acridine and phenanthridine.

In one embodiment, $(R_2)_3Sn(CR_3R_4)_nCO_2R_5$ is alkyl (tributylstannyl) acetate and $XCO_2R_6$ is alkyl or aryl chloroformate. The appropriate solvent for the invention is tetrahydrofuran, dimethoxyethane, dimethoxymethane, chloroform, methylene chloride, ether or dimethylsulfoxide. The preferred solvent is tetrahydrofuran.

The suitable reaction conditions are at a temperature of $-100°$ C. to $50°$ C. for a period of time from 1 minute to 24 hours. The preferred reaction conditions are at a temperature of $-50°$ C. to room temperature for a period of time from 5 minutes to 2 hours. More preferably, the reaction is carried out at a temperature of $-40°$ C. for 20 minutes and then warmed to room temperature over a fifteen minute period.

The invention herein is also directed to compounds having the structure:

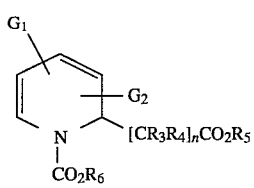

wherein each $G_1$ and $G_2$ may independently be H, with the proviso that $G_1$ and $G_2$ are not both H; CHO, biphenyl, benzhydryl, $R_1CO$ or aryl which may be unsubstituted or substituted with halogen, triflouromethyl, methoxy, nitro, amino, aldehyde, nitrile, ester, trimethylsilyl, triethylsilyl, tert-butyldimethylsilyl, triisopropylsilyl, trimethyltin, triethyltin, triisopropyltin; wherein $R_1$ may be $C_3$–$C_8$ cycloalkyl, thienyl, aryl, or furan which may be unsubstituted or substituted with halogen, $C_1$–$C_{16}$ alkyl which may be straight chain or branched, trifluoromethyl, methoxy, nitro, amino, aldehyde, nitrile, ester; wherein $R_3$, $R_4$ may be independently H, $C_1$–$C_{10}$ alkyl and $R_5$ may be $C_1$–$C_6$ straight chain or branched alkyl, aryl, 2,2,2-trichloroethyl, trimethylsilyl, tert-butyldimethylsilyl and n is an integer from 1 to 16; wherein $R_6$ may be a $C_1$–$C_6$ alkyl which may be straight chain or branched, aryl, benzyl, p-methoxybenzyl, allyl, trichloromethyl, menthyl (+ or –).

Specifically, the compounds may have the following structures:

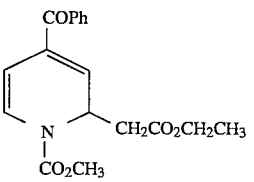

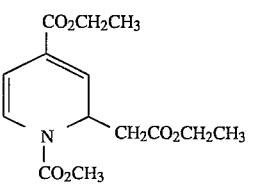

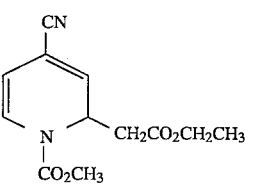

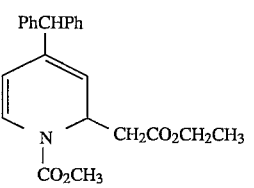

-continued

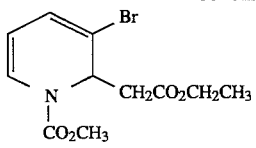
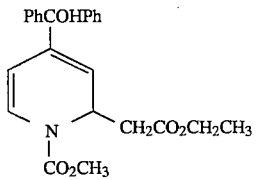
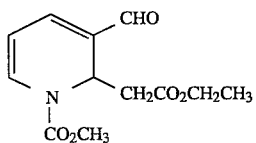
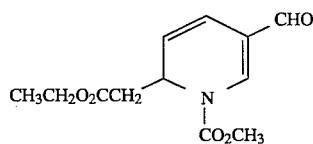

The compounds may also have the structure:

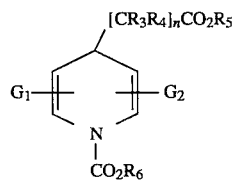

wherein $G_1$, $G_2$, $R_1$ $R_3$, $R_4$, $R_5$ and $R_6$ are as defined above.

Specifically, the compounds may have the structures:

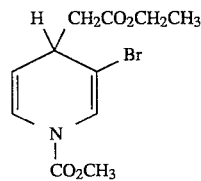
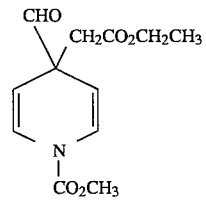

-continued

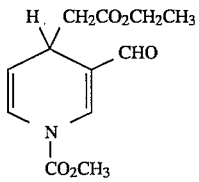

The invention is also directed to compounds having the structure:

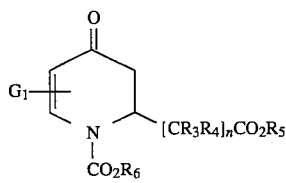

Specifically, the compound may have the structure:

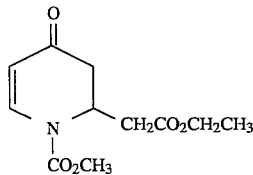

The invention is also directed to compounds having the structure:

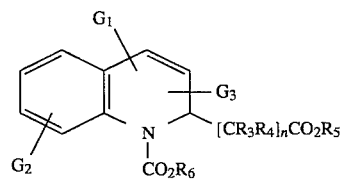

wherein
each $G_1$, $G_2$ and $G_3$ may independently be H, CHO, biphenyl, benzhydryl, $R_1CO$ or aryl which may be unsubstituted or substituted with halogen, triflouromethyl, methoxy, nitro, amino, aldehyde, nitrile, ester, trimethylsilyl, triethylsilyl, tert-butyldimethylsilyl, triisopropylsilyl, trimethyltin, triethyltin, triisopropyltin; wherein $R_1$ may be $C_3$–$C_8$ cycloalkyl, thienyl, aryl, or furan which may be unsubstituted or substituted with halogen, $C_1$–$C_6$ alkyl which may be straight chain or branched, trifluoromethyl, methoxy, nitro, amino, aldehyde, nitrile, ester; wherein $R_3$, $R_4$ may be independently H, $C_1$–$C_{10}$ alkyl and $R_5$ may be $C_1$–$C_6$ straight chain or branched alkyl, aryl, 2,2,2-trichloroethyl, trimethylsilyl, tert-butyldimethylsilyl and n is an integer from 1 to 16; wherein $R_6$ may be a $C_1$–$C_6$ alkyl which may be straight chain or branched, aryl, benzyl, p-methoxybenzyl, allyl, trichloromethyl, menthyl (+ or −).

Specifically, the compound may have the structure:

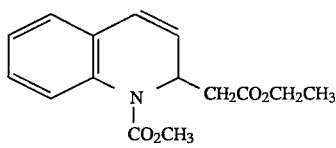

Alternatively, the compounds may have the structure:

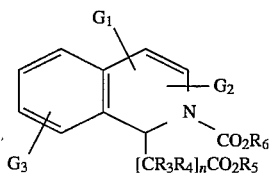

Specifically, the compounds may have the structure:

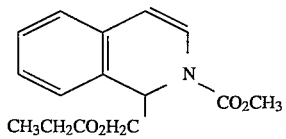

In addition, the compounds may have these structures:

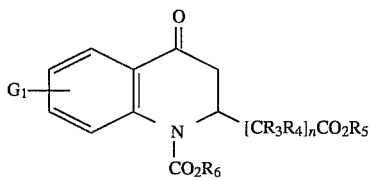

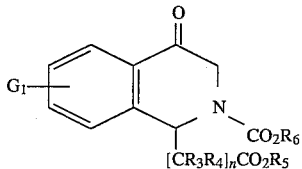

A general experimental procedure is as follows: to a solution of substituted pyridine (1 mmol) and ethyl (tributylstannyl)acetate (1 mmol) in THF (5 ml), at −40° C. was added methyl, benzyl or phenyl chloroformate (1 mmol) over a period of 5 min. The reaction mixture was stirred at −40° C. for 20 min and brought to room temperature over a period of 15 min. The reaction was then quenched by the addition of aq. ammonia (10 ml), partitioned between ethyl acetate and brine, dried over sodium or magnesium sulfate, concentrated and column purified to yield the corresponding carboethoxymethyl dihydropyridines listed in Table 1.

As is evident from Table 1, ketone, aldehyde, cyano, ester and bromo groups remain unaffected during the course of the reaction. Reaction of 4-benzoylpyridine with ethyl (tributylstannyl) acetate led to the desired 1,2 dihydropyridine in very high yield (Table 1, entry 2). This is in contrast to the Reformatsky reagent, which gave none of the desired product A on reaction with 4-benzoylpyridine. Instead, products corresponding to addition of the reagent to the acylpyridinium salt (1,2 addition) as well as to the carbonyl group were isolated (eq. 2). This clearly establishes the superiority of alkyl (trialkylstannyl) esters in general and specifically ethyl (tributylstannyl) acetate as the reagent of choice for carboethoxymethylation of functionalized pyridines.

TABLE 1

| Entry | | Yield (%)[b] | Ratio (A:B:C)[c] |
|---|---|---|---|
| 1 | R = $R_1$ = H | 87 | 75 (65):25 (21):0 |
| 2 | R = COPh; $R_1$ = H | 85 | 100:0:0 |
| 3 | R = $CO_2Et$; $R_1$ = H | 90 | 100:0:0 |
| 4 | R = CN; $R_1$ = H | 92 | 100:0:0 |
| 5 | R = H; $R_1$ = Br | 90 | 52 (47):48 (43):0 |
| 6 | R = CHO; $R_1$ = H | 10 | 0:100:0 |
| 7 | R = H; $R_1$ = CHO | 80 | 32:46 (37):22[d] |

[a]All compounds gave satisfactory spectral data. [b]Isolated yields. [c]Numbers in parenthesis refers to yields. [d]Combined Yield of A,C is 43%. Ratio of A,C is based on the integration of the methoxy signal in the $^1H$ NMR spectrum.

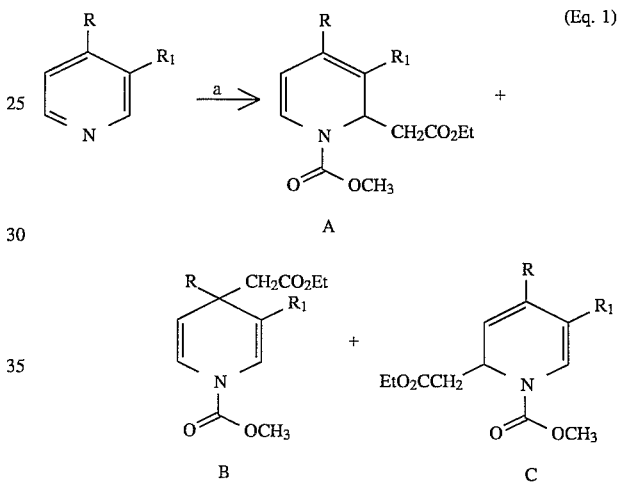

a = $Bu_3SnCH_2CO_2Et/ClCO_2CH_3$/−40° C. to RT/20 min

4-Methoxypyridine, a starting material widely used by Comins et. al., for the synthesis of a variety of N-heterocycles[9] gave a functionalized 1,2 dihydropyridone when subjected to the reaction conditions noted above (eq. 3). The reaction of quinolinium and isoquinolinium salts with ethyl (tributylstannyl)acetate led to the corresponding dihydroquinoline and isoquinoline adducts in very high yields (eq. 4,5). Attempted reaction of functionalized pyridines with ethyl(trimethylsilyl)acetate did not lead to the expected products. This was expected in view of the greater nucleophilicity of tin nucleophiles over silicon nucleophiles[10].

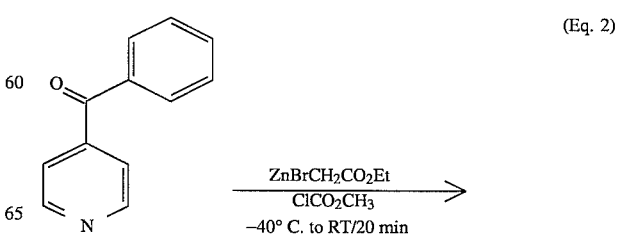

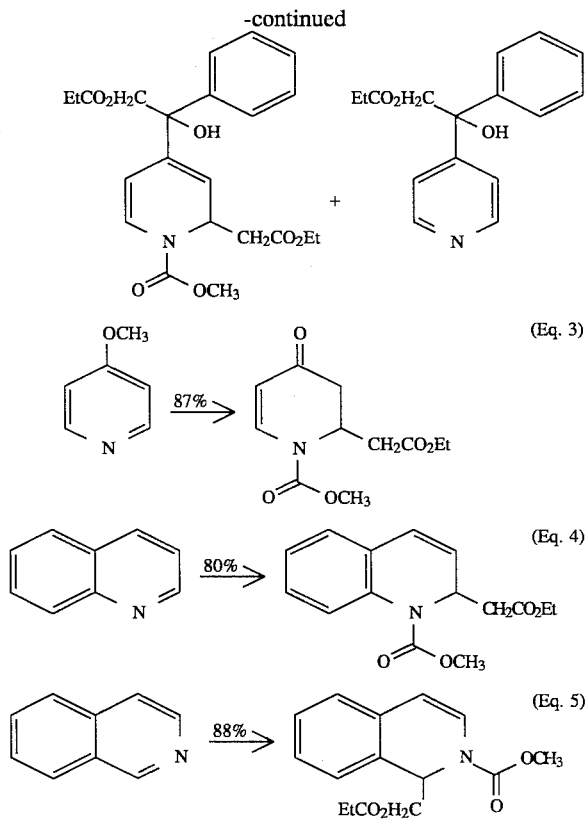

In conclusion, alkyl (trialkylstannyl) esters in general are versatile reagents for the carboalkoxyalkylation of functionalized pyridines. Specifically, the ethyl (tributylstannyl) acetate reagent can be made in bulk quantities, is very stable and can be stored for long periods of time unlike the corresponding Reformatsky reagent, which is not chemoselective, is moisture sensitive and has to be generated and used immediately.

The acetate and diene moieties of these functionalized 1,2-dihydropyridines, quinolines, isoquinolines, pyridones, quinolones and isoquinolones can serve as a useful handle that can be manipulated to generate a variety of N-heterocycles, such as those belonging to the indolizidine and quinolizidine group of alkaloids[11]. The method and compounds of this invention provide useful intermediates for preparing pharmaceutically active compounds. Applications for the pharmaceuticals include, treatment of epilepsy, diabetes and depression.

All compounds were characterized by $^1$H NMR spectra run in $CDCl_3$ on a GE QE plus 300 MHz instrument. Chemical shifts are expressed in parts per million ($\delta$ units) relative to internal tetramethylsilane ($\delta$ 0.0) or $CHCl_3$ ($\delta$7.26). Data are reported as follows: chemical shift, multiplicity (s= singlet, d=doublet, t=triplet, q=quartet, m=multiplet, bs=broad singlet, bd=broad doublet), coupling constant(s) and integration. Flash chromatography was carried out using silica gel (230–400 mesh, 60 Å).

4-Carboethoxymethyl-1-(methoxycarbonyl)-1,4-dihydropyridine (1B):

To a solution of pyridine (0.5 g, 6.3 mmol) and ethyl (tributylstannyl) acetate (2.38 g, 1 eq) in THF (10 mL), at –40° C. was added methyl chloroformate (0.9 mL, 1 eq) over a period of 5 min. The reaction mixture was stirred at –40° C. for 20 min, bought to room temperature over a period of 15 min and worked up as mentioned in the general experimental procedure. Elution with hexane/ethyl acetate (95:5 ml) gave the title compound as a oil (296 mg 21%). 1.26 (t, J=7.1 Hz, 3H), 2.39 (d, J=7.1 Hz, 2H), 3.4 (m, 1H), 3.8 (S, 3H), 4.15 (q, J=7.1 Hz, 2H), 4.8–4.95 (m, 2H), 6.8 (d, J=6 Hz, 2H).

2-Carboethoxymethyl- 1-(methoxycarbonyl)-1,2-dihydropyridine (1A):

Continued elution of the above reaction mixture with hexane/ethyl acetate gave the title compound as a oil (918 mg 65%). 1.26 (t, J=7.1 Hz, 3H), 2.4–2.65 (m, 2H), 3.8 (s, 3H) , 4.15 (q, J=7.1 Hz, 2H) , 5.1–5.4 (m, 2H) , 5.65 (bs, 1H), 5.9–6.1 (bs, 1H), 6.7 (d, J=6 Hz, 1H).

4-Benzoyl-2-carboethoxymethyl-1-(methoxycarbonyl)-1,2-dihydropyridine (2A):

To a solution of 4-benzoylpyridine (0.5 g, 2.7 mmol) and ethyl (tributylstannyl) acetate (1.02 g, 1 eq) in THF (10 ml), at –40° C. was added methyl chloroformate (0.21 ml, 1 eq) over a period of 5 min. The reaction mixture was stirred at –40° C. for 20 min, bought to room temperature over a period of 15 min and worked up as mentioned in the general experimental procedure. Elution with hexane/ethyl acetate (80:20) gave the title compound as a oil (674 mg 84%). 1.26 (t, J=7.1 Hz, 3H), 2.5–2.8 (m, 2H), 3.8 (s, 3H), 4.15 (q, J=7.1 Hz, 2H), 5.3-(m, 1H), 5.8–5.98 (bs, 1H), 6.25 (bd, 1H), 6.9 (d, J=6 Hz, 1H), 7.4–7.8 (m, 5H).

2-Carboethoxymethyl-4-ethoxyxcarbonyl-1-(methoxycarbonyl)-1,2-dihydropyridine (3A):

To a solution of ethyl isonicotinate (0.1 g, 0.66 mmol) and ethyl (tributylstannyl) acetate (0,249 g, 1 eq) in THF (10 ml), at –40° C. was added methyl chloroformate (0.094 ml, 1 eq) over a period of 5 min. The reaction mixture was stirred at –40° C. for 20 min, bought to room temperature over a period of 15 min and worked up as mentioned in the general experimental procedure. Elution with hexane/ethyl acetate (80:20) gave the title compound as a oil (175 mg 90%). 1.3 (m, 6H), 2.5–2.7 (m, 2H), 3.8 (s, 3H), 4.15 (q, J=7.1 Hz, 2H), 4.25 (m, 2H), 5.25–5.49 (m, 1H), 5.7–5.9 (bs, 1H), 6.65 (bs, 1H), 6.8 (d, J=6 Hz, 1H).

2-Carboethoxymethyl-4-cyano-1-(methoxycarbonyl)-1,2-dihydropyridine (4A):

To a solution of 4-cyanopyridine (0.25 g, 2.4 mmol) and ethyl (tributylstannyl) acetate (0.905 g, 1 eq) in THF (10 ml), at –40° C. was added methyl chloroformate (0.343 ml, 1 eq) over a period of 5 min. The reaction mixture was stirred at –40° C. for 20 min, bought to room temperature over a period of 15 min and worked up as mentioned in the general experimental procedure. Elution with hexane/ethyl acetate (80:20) gave the title compound as a oil (550 mg 92%). 1.26 (t, J=7.1 Hz, 3H), 2.5–2.8 (m, 2H), 3.8 (s, 3H), 4.15 (q, J=7.14 Hz, 2H), 5.25–5.5 (m, 2H), 6.4 (bs, 1H), 6.8 (d, J =6Hz, 1H).

3-Bromo-4-carboethoxymethl-1-(methoxycarbonyl)-1,4-dihydropyridine (5B):

To a solution of 4-cyanopyridine (0.2 g, 1.26 mmol) and ethyl (tributylstannyl) acetate (0.476 g, 1 eq) in THF (10 ml), at –40° C. was added methyl chloroformate (0.18 ml, 1 eq) over a period of 5 min. The reaction mixture was stirred at –40° C. for 20 min, bought to room temperature over a period of 15 min and worked up as mentioned in the general experimental procedure. Elution with hexane/ethyl acetate (80:20) gave the title compound as a oil (166 mg 43.2%). 1.26 (t, J=7.1 Hz, 3H), 2.4 (dd, J=15.7, 8.9 Hz, 1H), 2.9 (dd, J=15.7, 3.9 Hz, 1H), 3.6 (m, 1H), 3.8 (s, 3H), 4.15 (q, J=7.1 Hz, 2H), 5.0 (bs, 1H), 6.65–7.25 (m, 2H).

3-Bromo-2-carboethoxymethyl-1-(methoxycarbonyl)-1,2-dihydropyridine (5A):

Continued elution of the above reaction mixture with hexane/ethyl acetate gave the title compound as a oil (180 mg, 46.8%). 1.26 (t, 7.1 Hz, 3H), 2.58 (d, J=6.47 Hz, 2H), 3.8 (s, 3H), 4.15 (q, J=7.1 Hz, 2H), 5.2–5.45 (m, 2H), 6.3 (bs, 1H), 6.8 (d, J=6 Hz, 1H).

4-Carboethoxymethyl-4-formyl-1-(methoxycarbonyl)-1,4-dihydropyridine (6B):

To a solution of pyridine-4-carboxaldehyde (0.25 g, 2.33 mmol) and ethyl (tributylstannyl) acetate (0.879 g, 1 eq) in THF (10 ml ), at −40° C. was added methyl chloroformate (0.33 ml, 1 eq) over a period of 5 min. The reaction mixture was stirred at −40° C. for 20 min, bought to room temperature over a period of 15 min and worked up as mentioned in the general experimental procedure. Elution with hexane/ethyl acetate (90:10) gave the title compound as an oil (60 mg, 10%). 1.26 (t, J=7.1 Hz, 3H), 2.73 (s, 2H), 3.8 (s, 3H), 4.15 (q, J=7.1 Hz, 2H), 4.95 (bs, 1H), 7.0 (bd, 1H), 9.6 (s, 1H).

4-Carboethoxymethyl-3-formyl-1-1-(methoxycarbonyl)-1,4-dihydropyridine (7B):

To a solution of pyridine-3-carboxaldehyde (0.25 g, 2.33 mmol) and ethyl (tributylstannyl) acetate (0.879 g, 1 eq) in THF (10 ml), at −40° C. was added methyl chloroformate (0.33 ml, 1 eq) over a period of 5 min. The reaction mixture was stirred at −40° C. for 20 min, bought to room temperature over a period of 15 min and worked up as mentioned in the general experimental procedure. Elution with hexane/ethyl acetate (90:10) gave the title compound as an oil (220 mg, 37%). 1.26 (1.26t, J=7.1 Hz, 3H), 2.4 (dd, J=15.7 Hz, 8.9 Hz, 1H), 2.75 (dd, J=15.7, 3.92 Hz,1H), 3.75 (m, 1H), 3.8 (s, 3H), 4.15 (q, J=7.1 Hz, 2H), 5.25 (bs, 1H), 6.8 (bs, 1H), 7.7 (bs, 1H), 9.4 (s, 1H).

2-Carboethoxymethyl-3-formyl-1-(methoxycarbonyl)-1,2-dihydropyridine (7A) and 6-carboethoxymethyl-3-formyl-1-(methoxycarbonyl)-1,2-dihydropyridine (7C):

Continued elution of the above reaction mixture with hexane/ethyl acetate (90:10) gave the title compounds as a mixture (253 mg, 43%), the ratio of which was determined based on the integration of the methoxy signal in the $^1$H NMR spectrum. 1.26 (t, J=7.1 Hz, 6H), 2.35–2.65 (m, 4H), 3.8 (s, 3H), 3.9 (s, 3H), 4.0–4.2 (m, 4H), 5.25 (bs, 1H), 5.5–5.8 (m, 3H), 6.5 (d, J=9.9 Hz, 1H), 6.9 (bs, 1H), 7.6 (bs, 2H), 9.28 (s, 1H), 9.41 (s, 1H).

2-Carboethoxymethyl-4-diphenylmethyl-1-(methoxycarbonyl)-1,2-dihydropyridine (8A):

To a solution of diphenyl-4-pyridylmethane (0.5 g, 2.0 mmol) and ethyl (tributylstannyl) acetate (0,768 g, 1 eq) in THF (10 ml), at −40° C. was added methyl chloroformate (0.16 ml, 1 eq) over a period of 5 min. The reaction mixture was stirred at −40° C. for 20 min, bought to room temperature over a period of 15 min and worked up as mentioned in the general experimental procedure. Elution with hexane/ethyl acetate (85:15) gave the title compound as an oil (518 mg, 65%). 1.26 (t, J=7.1 Hz, 3H), 2.5–2.65 (m, 2H), 3.8 (s, 3H), 4.15 (q, J=7.1 Hz, 2H), 4.8 (s, 1H), 5.0–5.3 (m, 3H), 6.7 (d, J=6 Hz, 1H), 7.1–7.45 (m, 10H).

4-Benzhydryl-2-carboethoxymethyl-1-(methoxycarbonyl)-1,2-dihydropyridine (9A):

To a solution of 4-(pyridyl)benzhydrol (0.5 g, 1.9 mmol) and ethyl (tributylstannyl) acetate (0.721 g, 1 eq) in THF (10 ml), at −40° C. was added methyl chloroformate (0.15 ml, 1 eq) over a period of 5 min. The reaction mixture was stirred at −40° C. for 20 min, bought to room temperature over a period of 15 min and worked up as mentioned in the general experimental procedure. Elution with hexane/ethyl acetate (80:20) gave the title compound as an oil (665 mg, 85.5%). 1.26 (t, J=7.1 Hz, 3H), 2.49–2.61 (m, 2H), 2.75 (bs, 1H), 3.8 (s, 1H), 4.15 (q, 7.1 Hz, 2H), 5.1–5.4 (m, 3H), 6.7 (d, J=6 Hz, 1H), 7.2–7.4 (m, 10H).

2-Carboethoxymethyl-1-(methoxycarbonyl)-2,3-dihydropyridine-4-one (10):

To a solution of 4-methoxypyridine (0.5 g, 4.58 mmol) and ethyl (tributylstannyl) acetate (1.72 g, 1 eq) in THF (10ml), at −40° C. was added methyl chloroformate (0.36 ml, 1 eq) over a period of 5 min. The reaction mixture was stirred at 40° C. for 20 min, bought to room temperature over a period of 20 min. To the reaction mixture is then added 10% HCl (5 ml) and the contents stirred at room temperature for a further 10 min. The reaction is worked up as mentioned in the general experimental procedure. Elution with hexane/ethyl acetate (80:20) gave the title compound as a syrup. (957 mg, 87%). 1.26 (t, J=7.1 Hz, 3H), 2.5–2.7 (m, 3H), 2.88 (dd, J=16.9 Hz, 6.7 Hz, 1H), 3.8 (s, 1H) 4.15 (q, 7.1 Hz, 2H), 5.1 (bs, 1H), 5.35 (bs, 1H), 7.8 (bs, 1H).

2-Carboethoxymethyl-1-(methoxycarbonyl)-1,2-dihydroquinoline (11):

To a solution of quinoline (0.1 g, 0.77 mmol) and ethyl (tributylstannyl) acetate (0.291 g, 1 eq) in THF (10 ml), at −40° C. was added methyl chloroformate (0.11 ml, 1 eq) over a period of 5 min. The reaction mixture was stirred at −40° C. for 20 min, bought to room temperature over a period of 15 min and worked up as mentioned in the general experimental procedure. Elution with hexane/ethyl acetate (90:10) gave the title compound as an oil (170 mg, 80%). 1.26 (t, J=7.1 Hz, 3H), 2.42 (d, J=7.3 Hz, 2H), 3.8 (s, 1H), 4.1 (m, 2H), 5.45 (m, 1H), 6.1 (dd, J=5.9, 9.4 Hz, 1H), 6.5 (d, J =9.5 Hz, 1H), 7.09–7.3 (m, 3H), 7.6 (bs, 1H).

1-Carboethoxymethyl-2-(methoxycarbonyl)-1,2-dihydroisoquinoline (12):

To a solution of isoquinoline (0.1 g, 0.77 mmol) and ethyl (tributylstannyl) acetate (0.291 g, 1 eq) in THF (10 ml), at -40° C. was added methyl chloroformate (0.11 ml, 1 eq) over a period of 5 min. The reaction mixture was stirred at −40° C. for 20 min, bought to room temperature over a period of 15 min and worked up as mentioned in the general experimental procedure. Elution with hexane/ethyl acetate (90:10) gave the title compound as an oil (185 mg, 88%). The NMR spectrum indicated it to be a mixture of rotamers. 1.26 (m, 3H), 2.5–2.7 (m, 2H), 3.80 & 3.84 (2 s, 3H), 4.1 (m, 2H), 5.71 & 5.83 (2t, J=6.5 Hz, 1H), 5.89 & 5.9 (2d, J =7.6 Hz, 1H), 6.8 & 6.95 (2d, J=7.6 Hz, 1H), 7.05–7.3 (m, 4H).

References

1. Comins, D. L.; and O'Connor, S. Adv. Heterocycl.Chem. 1988, 44,199 and references cited therein.
2. a) Courtois, G.; Al-Arnaout, A.; and Miginiac, L. Tetrahedron Lett. 1985, 26, 1027. b) Comins, D. L., and Brown, J. D. Tetrahedron Lett. 1984, 25, 3297.
3. Yamaguchi, R.; Moriyasu, M.; Yoshioka, M.; and Kawanisi, M. J. Org. Chem. 1988, 53, 3507.
4 . For a simple and practical preparation of this reagent refer to Zapata, A.; and Acuna, A. C. Synth. Comm. 1984, 14, 27.
5. Comins, D. L.; and Abdullah, A. H. J. Org. Chem. 1982, 47, 4315.
6. Akiba, K.; Iseki, Y.; and Wada, M. Bull. Chem. Soc. Jpn. 1984, 57, 1994.
7. Pearson, R. G. J. Chem. Educ. 1968, 45, 581, 643.
8. Sundberg, R. J; Hamilton, G.; and Trindle, C. J. Org. Chem. 1986, 51, 3672.
9. Comins, D. L.; and Al-awar, S. R. J. Org. Chem. 1992, 57, 4098 and references cited therein.
10. Hosomi, A.; Iguchi, H.; Endo, M.; and Sakurai, H. Chem. Lett. 1979, 977.
11. Michael, J. P. Nat. Prod. Rep. 1991, 553 and references cited therein.

What is claimed is:

1. A method of preparing a 1,2-dihydropyridine compound having the structure:

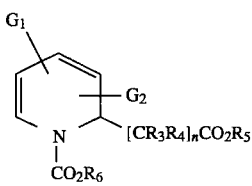

wherein each $G_1$ and $G_2$ may independently be H, CHO, biphenyl, benzhydryl, $R_1CO$ or aryl which may be unsubstituted or substituted with halogen, trifluromethyl, methoxy, nitro, amino, aldehyde, nitrile, ester, trimethylsilyl, triethylsilyl, tert-butyldimethylsilyl, triisopropylsilyl, trimethyltin, triethyltin, triisopropyltin; wherein $R_1$ may be $C_3$–$C_8$ cycloalkyl, thienyl, aryl, or furan which may be unsubstituted or substituted with halogen, $C_1$–$C_{16}$ alkyl which may be straight chain or branched, trifluoromethyl, methoxy, nitro, amino, aldehyde, nitrile, ester; wherein $R_3$, $R_4$ may be independently H, $C_1$–$C_{10}$ alkyl and $R_5$ may be $C_1$–$C_6$ straight chain or branched alkyl, aryl, 2,2,2-trichloroethyl, trimethylsilyl, tert-butyldimethylsilyl and n is an integer from 1 to 16; wherein $R_6$ may be a $C_1$–$C_6$ alkyl which may be straight chain or branched, aryl, benzyl, p-methoxybenzyl, allyl, trichloromethyl, menthyl (+ or –)

which comprises reacting a compound having the structure:

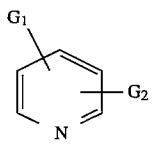

wherein $G_1$ and $G_2$ are as defined above;

with a compound having the structure:

wherein $R_2$ may be a $C_1$–$C_4$ alkyl which may be straight chain or branched and n, $R_3$, $R_4$, $R_5$ are as defined above;

and with a compound having the structure:

wherein

X may be a halogen and $R_6$ is as defined above; under suitable reaction conditions and in an appropriate solvent so as to form the 1,2-dihydropyridine compound.

2. The method of claim 1, wherein the appropriate solvent is tetrahydrofuran, dimethoxyethane, dimethoxymethane, chloroform methylene chloride, ether or dimethylsulfoxide.

3. The method of claim 1, wherein the appropriate solvent is tetrahydrofuran.

4. The method of claim 1, wherein the suitable reaction conditions are at a temperature of –100° C. to 50° C. for a period of time from 1 minute to 24 hours.

5. The method of claim 1, wherein the suitable reaction conditions are at a temperature of –50° C. to room temperature for a period of time from 5 minutes to 2 hours.

6. The method of claim 1, wherein $(R_2)_3Sn(CR_3R_4)_nCO_2R_5$ is alkyl (tributylstannyl) acetate.

7. The method of claim 1, wherein $XCO_2R_6$ is alkyl or aryl chloroformate.

8. A method of preparing a 1,2-dihydroquinoline compound having the structure:

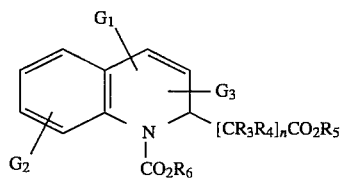

wherein each $G_1$, $G_2$ and $G_3$ may independently be H, CHO, biphenyl, benzhydryl, $R_1CO$ or aryl which may be unsubstituted or substituted with halogen, triflouromethyl, methoxy, nitro, amino, aldehyde, nitrile, ester, trimethylsilyl, triethylsilyl, tert-butyldimethylsilyl, triisopropylsilyl, trimethyltin, triethyltin, triisopropyltin; wherein $R_1$ may be $C_3$–$C_8$ cycloalkyl, thienyl, aryl, or furan which may be unsubstituted or substituted with halogen, $C_1$–$C_{16}$ alkyl which may be straight chain or branched, trifluoromethyl, methoxy, nitro, amino, aldehyde, nitrile, ester); wherein $R_3$, $R_4$ may be independently H, $C_1$–$C_{10}$ alkyl and $R_5$ may be $C_1$–$C_6$ straight chain or branched alkyl, aryl, 2,2,2-trichloroethyl, trimethylsilyl, tert-butyldimethylsilyl and n is an integer from 1 to 16; wherein $R_6$ may be a $C_1$–$C_6$ alkyl which may be straight chain or branched, aryl, benzyl, p-methoxybenzyl, allyl, trichloromethyl, menthyl (+ or –), which comprises reacting a compound having the structure:

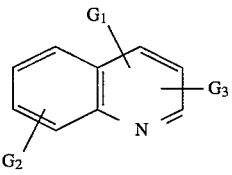

wherein $G_1$, $G_2$ and $G_3$ are as defined above; with a compound having the structure:

wherein $R_2$ may be a $C_1$–$C_4$ alkyl which may be straight chain or branched and n, $R_3$, $R_4$, $R_5$ are as defined above;

and with a compound having the structure:

wherein

X may be a halogen and $R_6$ is as defined above; under suitable reaction conditions and in an appropriate solvent so as to form the 1,2-dihydroquinoline compound.

9. The method of claim 8, wherein the appropriate solvent is tetrahydrofuran, dimethoxyethane, dimethoxymethane, chloroform, methylene chloride, ether or dimethylsulfoxide.

10. The method of claim 8, wherein the appropriate solvent is tetrahydrofuran.

11. The method of claim 8, wherein the suitable reaction conditions are at a temperature of −100° C. to 50° C. for a period of time from 1 minute to 24 hours.

12. The method of claim 8, wherein the suitable reaction conditions are at a temperature of −50° C. to room temperature for a period of time from 5 minutes to 2 hours.

13. The method of claim 8, wherein $(R_2)_3Sn(CR_3R_4)_nCO_2R_5$ is alkyl (tributylstannyl) acetate.

14. The method of claim 8, wherein $XCO_2R_6$ is alkyl or aryl chloroformate.

15. A method of preparing a 1,2-dihydroisoquinoline compound having the structure:

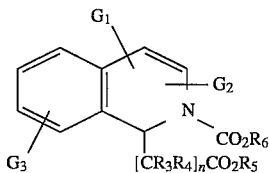

wherein
each $G_1$, $G_2$ and $G_3$ may independently be H, CHO, biphenyl, benzhydryl, $R_1CO$ or aryl which may be unsubstituted or substituted with halogen, triflouromethyl, methoxy, nitro, amino, aldehyde, nitrile, ester, trimethylsilyl, triethylsilyl, tert-butyldimethylsilyl, triisopropylsilyl, trimethyltin, triethyltin, triisopropyltin; wherein $R_1$ may be $C_3$–$C_8$ cycloalkyl, thienyl, aryl, or furan which may be unsubstituted or substituted with halogen, $C_1$–$C_{16}$ alkyl which may be straight chain or branched, trifluoromethyl, methoxy, nitro, amino, aldehyde, nitrile, ester; wherein $R_3$, $R_4$ may be independently H, $C_1$–$C_{10}$ alkyl and $R_5$ may be $C_1$–$C_6$ straight chain or branched alkyl, aryl, 2,2,2-trichloroethyl, trimethylsilyl, tert-butyldimethylsilyl and n is an integer from 1 to 16; wherein $R_6$ may be a $C_1$–$C_6$ alkyl which may be straight chain or branched, aryl, benzyl, p-methoxybenzyl, allyl, trichloromethyl, menthyl (+ or −), which comprises reacting a compound having the structure:

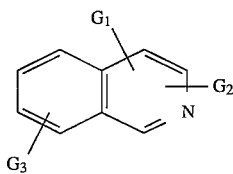

wherein
$G_1$, $G_2$ and $G_3$ are as defined above;
with a compound having the structure:

wherein
$R_2$ may be a $C_1$–$C_4$ alkyl which may be straight chain or branched and n, $R_3$, $R_4$, $R_5$ are as defined above;
and with a compound having the structure:

$XCO_2R_6$ wherein
X may be a halogen and $R_6$ is as defined above;
under suitable reaction conditions and in an appropriate solvent so as to form the 1,2-dihydroisoquinoline compound.

16. The method of claim 15, wherein the appropriate solvent is tetrahydrofuran, dimethoxyethane, dimethoxymethane, chloroform, methylene chloride, ether or dimethylsulfoxide.

17. The method of claim 15, wherein the appropriate solvent is tetrahydrofuran.

18. The method of claim 15, wherein the suitable reaction conditions are at a temperature of −100° C. to 50° C. for a period of time from 1 minute to 24 hours.

19. The method of claim 15, wherein the suitable reaction conditions are at a temperature of −50° C. to room temperature for a period of time from 5 minutes to 2 hours.

20. The method of claim 15, wherein $(R_2)_3Sn(CR_3R_4)_nCO_2R_5$ is alkyl (tributylstannyl) acetate.

21. The method of claim 15, wherein $XCO_2R_6$ is alkyl or aryl chloroformate.

22. A method of preparing a 1,2-dihydropyridone compound having the structure:

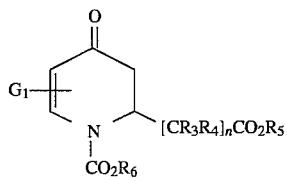

wherein
each $G_1$ may be H, CHO, biphenyl, benzhydryl, $R_1CO$ or aryl which may be unsubstituted or substituted with halogen, triflouromethyl, methoxy, nitro, amino, aldehyde, nitrile, ester, trimethylsilyl, triethylsilyl, tert-butyldimethylsilyl, triisopropylsilyl, trimethyltin, triethyltin, triisopropyltin; wherein $R_1$ may be $C_3$–$C_8$ cycloalkyl, thienyl, aryl, or furan which may be unsubstituted or substituted with halogen, $C_1$–$C_{16}$ alkyl which may be straight chain or branched, trifluoromethyl, methoxy, nitro, amino, aldehyde, nitrile, ester; wherein $R_3$, $R_4$ may be independently H, $C_1$–$C_{10}$ alkyl and $R_5$ may be $C_1$–$C_6$ straight chain or branched alkyl, aryl, 2,2,2-trichloroethyl, trimethylsilyl, tert-butyldimethylsilyl and n is an integer from 1 to 16 ; wherein $R_6$ may be a $C_1$–$C_6$ alkyl which may be straight chain or branched aryl, benzyl, p-methoxybenzyl, allyl, trichloromethyl, methyl (+ or −)

which comprises reacting a compound having the structure:

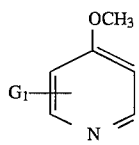

wherein
$G_1$ is as defined above;
with a compound having the structure:

wherein
R$_2$ may be a C$_1$–C$_4$ alkyl which may be straight chain or branched and n, R$_3$, R$_4$, R$_5$ are as defined above;

and with a compound having the structure:

XCO$_2$R$_6$ where
X may be a halogen and R$_6$ is as defined above; under suitable reaction conditions and in an appropriate solvent so as to form the 1,2-dihydropyridone compound.

23. The method of claim 22, wherein the appropriate solvent is tetrahydrofuran, dimethoxyethane, dimethoxymethane, chloroform, methylene chloride, ether or dimethylsulfoxide.

24. The method of claim 22, wherein the appropriate solvent is tetrahydrofuran.

25. The method of claim 22, wherein the suitable reaction conditions are at a temperature of −100° C. to 50° C. for a period of time from 1 minute to 24 hours.

26. The method of claim 22, wherein the suitable reaction conditions are at a temperature of −50° C. to room temperature for a period of time from 5 minutes to 2 hours.

27. The method of claim 22, wherein (R$_2$)$_3$Sn(CR$_3$R$_4$)$_n$CO$_2$R$_5$ is alkyl (tributylstannyl) acetate.

28. The method of claim 22, wherein XCO$_2$R$_6$ is alkyl or aryl chloroformate.

29. A method of preparing a 1,2-dihydroquinolone compound having the structure:

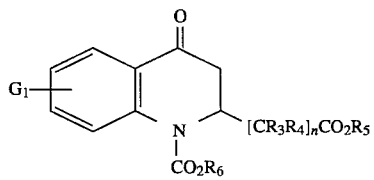

wherein
G$_1$ may H, CHO, biphenyl, benzhydryl, R$_1$CO or aryl which may be unsubstituted or substituted with halogen, triflouromethyl, methoxy, nitro, amino, aldehyde, nitrile, ester, trimethylsilyl, triethylsilyl, tert-butyldimethylsilyl, triisopropylsilyl, trimethyltin, triethyltin, triisopropyltin; wherein R$_1$ may be C$_3$–C$_8$ cycloalkyl, thienyl, aryl, or furan which may be unsubstituted or substituted with halogen, C$_1$–C$_{16}$ alkyl which may be straight chain or branched, trifluoromethyl, methoxy, nitro, amino, aldehyde, nitrile, ester; wherein R$_3$, R$_4$ may be independently H, C$_1$–C$_{10}$ alkyl and R$_5$ may be C$_1$–C$_6$ straight chain or branched alkyl, aryl, 2,2,2-trichloroethyl, trimethylsilyl, tert-butyldimethylsilyl and n is an integer from 1 to 16; wherein R$_6$ may be a C$_1$–C$_6$ alkyl which may be straight chain or branched, aryl, benzyl, p-methoxybenzyl, allyl, trichloromethyl, methyl (+ or −)

which comprises reacting a compound having the structure:

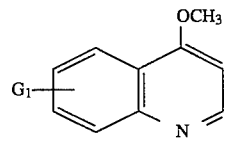

wherein
G$_1$ is as defined above;
with a compound having the structure:

(R$_2$)$_3$Sn(CR$_3$R$_4$)$_n$CO$_2$R$_5$ wherein
R$_2$ may be a C$_1$–C$_4$ alkyl which may be straight chain or branched and n, R$_3$, R$_4$, R$_5$ are as defined above;

and with a compound having the structure:

XCO$_2$R$_6$ wherein
X may be a halogen and R$_6$ is as defined above; under suitable reaction conditions and in an appropriate solvent so as to form the 1,2-dihydroquinolone compound.

30. The method of claim 29, wherein the appropriate solvent is tetrahydrofuran, dimethoxyethane, dimethoxymethane, chloroform, methylene chloride, ether or dimethylsulfoxide.

31. The method of claim 29, wherein the appropriate solvent is tetrahydrofuran.

32. The method of claim 29, wherein the suitable reaction conditions are at a temperature of −100° C. to 50° C. for a period of time from 1 minute to 24 hours.

33. The method of claim 29, wherein the suitable reaction conditions are at a temperature of 50° C. to room temperature for a period of time from 5 minutes to 2 hours.

34. The method of claim 29, wherein (R$_2$)$_3$Sn(CR$_3$R$_4$)$_n$CO$_2$R$_5$ is alkyl (tributylstannyl) acetate.

35. The method of claim 29, wherein XCO$_2$R$_6$ is alkyl or aryl chloroformate.

* * * * *

UNITED STATES PATENT AND TRADEMARK OFFICE
CERTIFICATE OF CORRECTION

PATENT NO. : 5,453,509
DATED : September 26, 1995
INVENTOR(S) : T.G. Murali Dhar, Charles Gluchowski It is certified that error appears in the above-identified patent and that said Letters Patent is hereby corrected as shown below:

Title page, Abstract line 40: Insert "with $(R_2)_3Sn(CR_3R_4)nCO_2R_5$ and $XCO_2R_6$" before the paragraph "The reaction is performed.."

Col.10, line 30: "(0,249 g, 1 eq)" should read --(0.249 g, 1 eq)--

Col.11, lines 18-19: "4-Carboethoxymethyl-3-formyl-1-1-(methoxycarbonyl)-1,4-dihydropyridine" should read --4-Carboethoxymethyl-3-formyl-1-(methoxycarbonyl)-1,4-dihydropyridine-- line 45: "(0,768 g, 1 eq)" should read --(0.768 g, 1 eq)--

Signed and Sealed this

Twenty-seventh Day of October, 1998

Attest:

BRUCE LEHMAN

Attesting Officer

Commissioner of Patents and Trademarks